United States Patent [19]

Anderson et al.

[11] Patent Number: 4,723,014

[45] Date of Patent: Feb. 2, 1988

[54] PROCESS FOR THE PREPARATION OF 2-SUBSTITUTED-1,4-DIHYDROPYRIDINES

[75] Inventors: Kevin R. Anderson, Cedar Rapids, Iowa; Ila Sircar, Ann Arbor, Mich.

[73] Assignee: Warner-Lambert Company, Morris Plains, N.J.

[21] Appl. No.: 932,751

[22] Filed: Nov. 19, 1986

[51] Int. Cl.[4] .................. C07D 211/84; C07D 471/04; C07D 417/00; C07D 413/00
[52] U.S. Cl. .................................. 546/286; 546/165; 546/112; 546/183; 546/272; 546/273; 546/278; 546/281; 546/321; 546/322; 544/61; 544/60; 544/127; 544/128; 544/124; 544/360; 544/362; 544/363
[58] Field of Search ............... 546/165, 183, 286, 322, 546/112, 321, 273, 272, 281, 278; 544/61, 60, 127, 128, 124, 360, 362, 363

[56] References Cited

U.S. PATENT DOCUMENTS 4,567,268 1/1986 Young ............................... 546/116

FOREIGN PATENT DOCUMENTS

WO87/00836 12/1987 PCT Int'l Appl. ................. 546/116

*Primary Examiner*—Alan L. Rotman
*Assistant Examiner*—J. Richter
*Attorney, Agent, or Firm*—Joan Thierstein

[57] ABSTRACT

The present invention provides a process for preparing a 2-substituted-1,4-dihydropyridine by providing a regiospecific bromine containing intermediate which is then reacted with a nucleophile to provide a wide range of substituents at the 2-position of 1,4-dihydropyridines. Also the present invention is novel 3-substituted-1,4-dihydropyridines having cardiovascular activity.

9 Claims, No Drawings

PROCESS FOR THE PREPARATION OF 2-SUBSTITUTED-1,4-DIHYDROPYRIDINES

BACKGROUND OF THE INVENTION

The present invention is a process for preparing 2-substituted-1,4-dihydropyridines, useful as cardiovascular agents.

U.S. Pat. No. 4,567,268 reports a pyridinium bromide perbromide and NBS as a bromine generator for use in a process to form an internal ester, i.e. lactone, such as tetrahydrofuro(3,4-b)pyridine from a 3,5-diester-1,4-dihydropyridine. However, surprisingly it is now found that a pyridinium bromide perbromide provides a regiospecific brominated intermediate, i.e. having a bromine containing substituent at the 2-position in a 1,4-dihydropyridine. The intermediate, thus, is further reacted with a nucleophile to provide a wide range of 2-substituted-1,4-dihydropyridines in high yields heretofore available only through a complex three part Hantzsch reaction having low yields of products requiring extensive chromatographic separation.

Additionally selected novel 2-substituted-1,4-dihydropyridines having calcium blocking activity are the present invention.

SUMMARY OF THE INVENTION

The present invention is a process for the preparation of compounds of the formula (I)

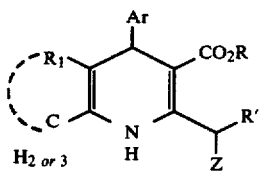

wherein Ar is aryl or heteroaryl;
R' is hydrogen, lower alkyl or aryl;
R is straight or branched hydrocarbon chain of from two through six carbons;
$R_1$ is CN, $CO_2R_3$ wherein $R_3$ is lower alkyl, or is taken together with - - -, which is an optional bond to form a fused ring with the dihydropyridine wherein the fused ring is of the formula

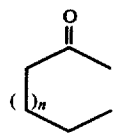

where n is 0 or 1 and Z is
(1) $A-R_2$ wherein A is O or S and $R_2$ is
  (i) alkyl, straight or branched, optionally substituted by (a) hydroxy, (b) alkoxy, (c) $NR_3R_4$ wherein $R_3$ and $R_4$ are independently hydrogen or lower alkyl; (d) $S(O)_nR_5$ wherein n is zero, one or two and $R_5$ is lower alkyl, aryl, aralkyl wherein ar is aryl and alkyl is an alkylenyl linkage straight or branched having of from one to four carbons, or heteroaryl with the proviso that $R_2$ is not $S(O)_n$ when A is S; or (e) $CO_2R_4$ wherein $R_4$ is hydrogen or lower alkyl;
  (ii) aryl;
  (iii) heteroaryl; or (iv)

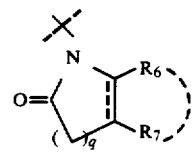

wherein q is one or two, and - - - is an optional bond; $R_6$ and $R_7$ are independently hydrogen, alkyl of from one to four carbons, alkenyl of from two to four carbons, or taken together with - - - $R_6$ and $R_7$ form

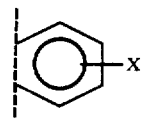

wherein X is halogen, lower alkyl, trifluoromethyl, nitro, amino, mono- or di-lower alkylamino, cyano, lower alkoxy, lower alkylthio, and the like;

(2) $NR_3R_4$ wherein $R_3$ and $R_4$ are independently hydrogen or lower alkyl; or (3)

wherein Y is O, S, $CH_2$, CHAr wherein Ar is independently aryl, or $NR_5$ wherein $R_5$ is independently as defined above;

(4)

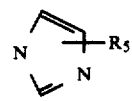

wherein $R_5$ is independently as defined above;
which comprises treating a compound of the formula (II)

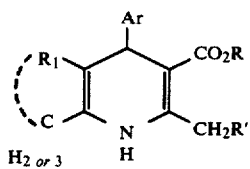

wherein Ar, R, R', and $R_1$ are as defined above; with pyridinium bromide perbromide in a solvent to obtain an intermediate of the formula (III)

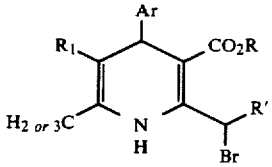

wherein Ar, R₁, R', and R is as defined above; and then reacting the compound of formula III with a compound of the formula HZ wherein Z is as defined above, to obtain the compound of formula I above.

Since the process can be performed as a one pot process the invention is also the preparation of a compound of formula I as defined above which comprises treating a compound of formula II as defined above with pyridinium bromide perbromide followed by treating with the compound of formula HZ to obtain a compound of the formula I.

The present invention is also for novel compounds of the formula (X)

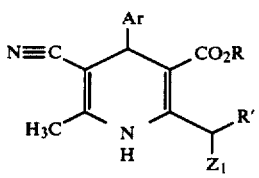

and pharmaceutically acceptable salts thereof; wherein Ar, R' and R are independently as defined above and $Z_1$ is

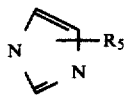

wherein $R_5$ is independently as defined above; or

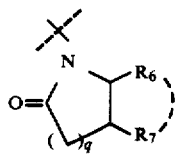

wherein q, $R_6$ and $R_7$ are as defined above.

The novel compounds of formula X are calcium antagonist useful, for example, as cardiovascular agents in a manner analogous to the calcium channel blocker compounds of U.S. Ser. No. 852,731 filed Apr. 21, 1986 which a continuation in part of U.S. Ser. No. 745965 filed June 17, 1985 and is therefore, incorporated by reference herein.

Thus, the present invention is also a pharmaceutical composition for use in treating cardiovascular diseases comprising a cardiovascular effective amount of the compound of formula X as defined above with a pharmaceutically acceptable carrier.

The present invention is also a method of treating cardiovascular disease in mammals, particularly humans, suffering therefrom which comprises administering to such mammals the compound of formula X as defined above.

The compounds of formula X are useful as salts derived from physiologically acceptable acids. The acids may be mineral acids such as hydrochloric acid, sulfuric acid, and the like, or organic acids, such as ethanesulfonic acid, benzenesulfonic acid, p-toluenesulfonic acid, and the like; giving the hydrochloride, sulfamate, ethanesulfonate, benzenesulfonate, p-toluenesulfonate, and the like, respectively. See Berge et al, "Pharmaceutical Salts" in *J. of Pharmaceutical Sciences*, January, 1977, Vol. 66, No. 1, pp 1–19.

The compound of formula X of the present invention includes stereoisomers due to the presence of at least one asymmetric carbon atom at the four position of the 1,4-dihydropyridine nucleus and can exist as each optical isomer or a racemic mixture. Further, some of the compounds of formula X which have not less than two asymmetric carbon atoms in its molecule may exist as each diastereomer(s) or the mixture thereof. The mixture of the diastereomers can be resolved to each racemic compound by conventional resolution methods such as chromatography or fractional recrystallization and the like and the racemic compound can be resolved into each optical isomer by a conventional method for racemic resolution by fractional recrystallization of a salt of the racemic compound with an optically active acid, e.g., tartaric acid or camphor sulfonic acid.

The terms "stereoisomers" and "stereoisomerism" as used throughout this specification and the appended claims are to be given the meaning usually ascribed to them by practitioners of the organic chemical arts, and specifically as defined by Eliel in "Stereochemistry of Carbon Compounds," pp 1–6, McGraw-Hill, New York, 1962.

The salts of the compounds of formula X; possible when a basic nitrogen is present, are prepared in a manner which is in itself known by reacting the compounds obtained according to the processes of the invention with suitable acids. For example, the appropriate compounds of formula X are dissolved in ethanol, then suitable acids are added to the solution.

Examples of inorganic and organic acids which form physiologically acceptable acid addition salts with the dihydropyridines of the present invention are hydrogen halide acids, such as hydrochloric acid and hydrobromic acid, particularly hydrochloric, phosphoric, sulfuric, nitric, monofunctional and bifunctional carboxylic acids and hydroxycarboxylic acids, such as acetic, maleic, succinic, fumaric, tartaric, citric, salicylic, lactic, and 1,5-naphthalenedicarboxylic and naphthalenedicarboxylic and naphthalenedisulphonic acids.

DETAILED DESCRIPTION OF THE INVENTION

"Lower alkyl" as used herein means a hydrocarbon chain of from one to six carbons, such as methyl, ethyl, propyl, butyl, pentyl or hexyl and isomers thereof.

The term "aryl" as used herein means phenyl, optionally substituted with one or two of lower alkyl, halogen, trifluoromethyl, nitro, amino, mono- or di-lower alkylamino, cyano, lower alkoxy, lower thioalkyl and the like.

The term "heteroaryl" as used herein means thienyl, furyl, pyryl, pyridinyl, quinolyl, isoquinolyl, pyrimidyl, pyradazinyl, quinazolyl, quinoxalyl, benzothienyl, pyrazolyl, imidazolyl, oxazolyl, isoxazolyl, thiazolyl, triazolyl, pyrazinyl, oxazinyl, thiazinyl, indolizinyl, indolyl, benzofuranyl, benzioxazolyl, benthiazolyl, benztriazolyl, benzoxadiazolyl, cinnobinyl, phthalaxinyl, naphthyridinyl, or benzothiazinyl.

"Halogen" in the present invention means fluorine, chlorine, or bromine.

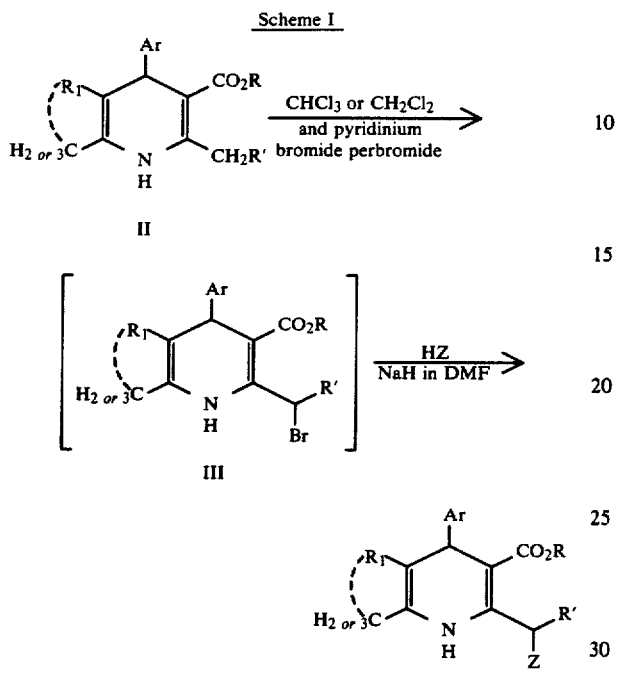

wherein R, R', R₁, Ar and Z are as defined above.

Generally, the process of the present invention as shown in Scheme I is carried out in a dry inert solvent, such as trichloromethane, dichloromethane, chloroform, or the like. Water or ethanol and the like can be removed from the medium by standard methods. Further, the process is carried out in the presence of pyridine.

Thus, from at least one equivalent to an excess, such as up to two equivalents, of pyridinium bromide perbromide is added to a mixture of a compound of the formula II in a solvent such as chloroform, methylene chloride and the like. The mixture also contains pyridine or triethylamine, preferably pyridine, in an amount preferably from one equivalent to an excess of equivalents. The mixture is maintained at a temperature from approximately −50° C. to 20° C. preferably −10° to 0° C. The mixture is stirred until flash chromatography over silica gel (10% ethanol/dichloroethane) indicates a formation of compound of the formula III. The compound of formula III may be isolated for further reaction or the compound of formula III may be further reacted without separation from the reaction mixture.

The compound of formula III is thus, contacted with a compound of the formula HZ by using a reaction mixture and conditions appropriate to the presence of formation of the moiety of the formula Z. For example, a solvent, such as tetrahydrofuran (THF), N,N-dimethylformamide or the like, may be added to the compound of formula III or the mixture containing the formula III. Then, the solution or mixture of formula III is added to the HZ or a compound providing the Z moiety in a solvent such as one or more of tetrahydrofuran or dimethylformamide and the like preferably in the presence of, for example, sodium hydride if appropriate to the formation of the Z moiety. The resulting reaction mixture is prepared at from −20° C. to 0° C. and then warmed to room temperature. Then it is stirred until appropriate chromatography indicates the formation of the compound of formula I, approximately an hour for most reactions.

Compounds of formula I may be separated including purification from the reaction mixture by conventional means such as extraction, distillation, chromatography, and the like. Further, the compounds of formula I which are stereoisomers having at least one asymmetric carbon or diastereomers having not less than two asymmetric carbon can be resolved to each racemate by conventional means such as chromatography or fractional recrystallization and the like and the racemate can be resolved into each optical isomer by a conventional racemic resolution by fractional recrystallization of a salt of the racemic compound with an optically active acid, e.g. tartaric acid or camphor sulfonic acid.

The starting materials i.e. the compounds of the formula II as defined above for the process of the present invention are readily available, are known or can be prepared by known methods.

For example, the following Scheme II illustrates one such known process for preparing the starting materials.

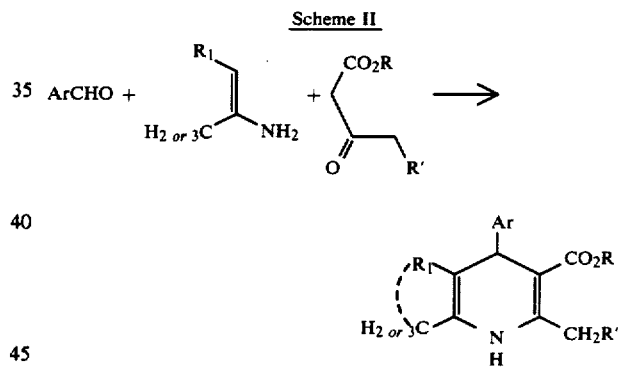

wherein Ar, R', R₁, and R are as defined above.

Further, it is understood that optionally additional steps to those described for Scheme I may be used to provide derivatives which are previously known compounds. See, for example U.S. Ser. No. 852,731, cited above, for methods shown as the final step shown therein, such as, for example, the following Schemes III and IV:

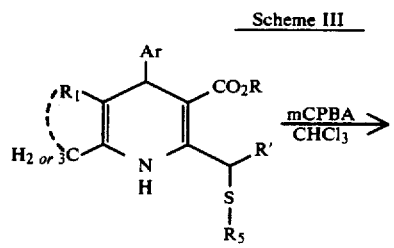

-continued
Scheme III

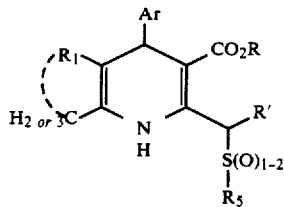

wherein Ar, R, R', R₁, and R₅ are as defined above.

ment of congestive heart failure, coronary heart disease, myocardial ischemia, angina, and hypertension.

It is reasonable to believe the compounds of formula X inhibit nitrendipine in an assay as described in U.S. Ser. No. 852,731 which is incorporated by reference above.

Accordingly, the present invention includes a method for treating mammals, including humans, suffering from the diseases noted above by administering to such mammals a corresponding pharmaceutical composition containing a compound of the formula X as defined above in appropriate unit dosage form. A physi-

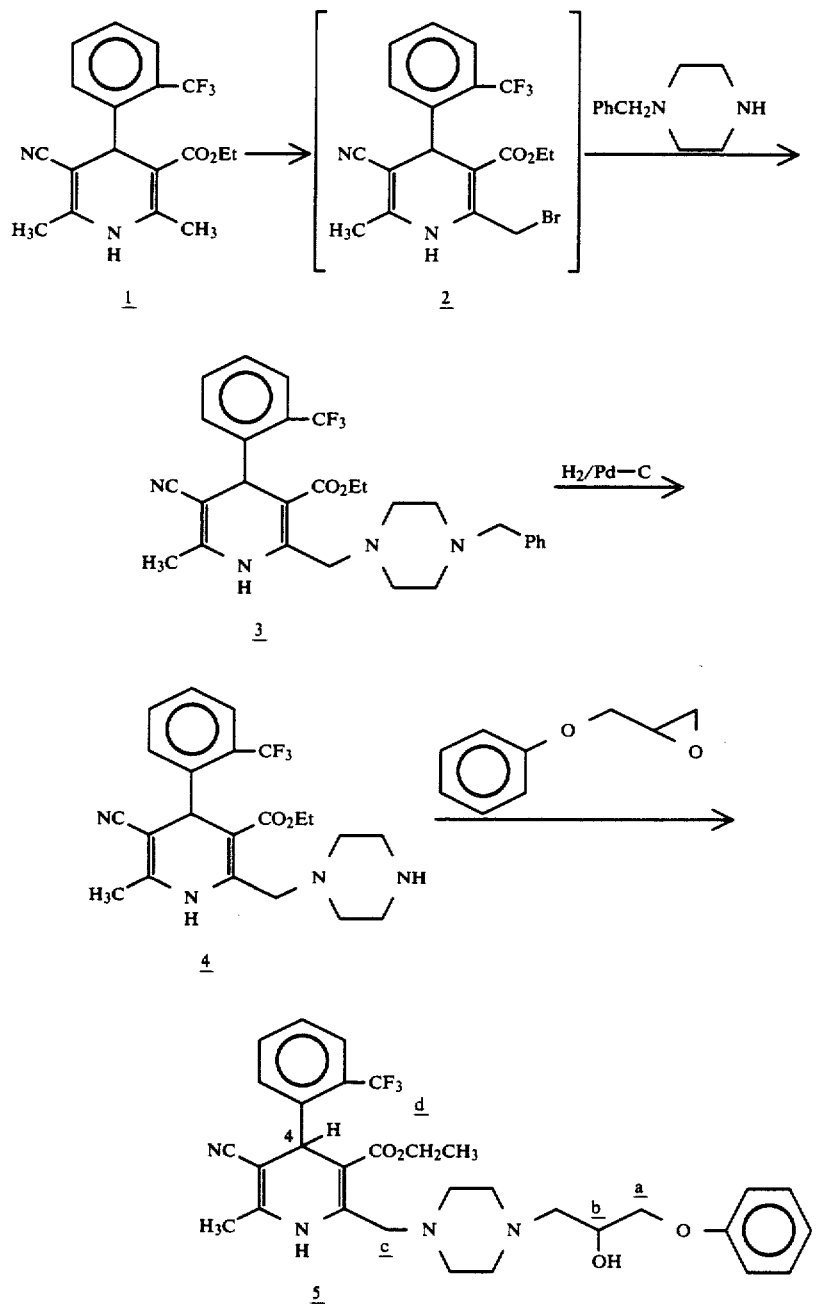

The novel compounds of the formula X as defined above possess vasodilatory activity useful for the treatment cian or veterinarian of ordinary skill readily determines a subject exhibiting symptoms of the diseases. The routes of administration and the dosage forms therefor are from among those conventional to the pharmaceutical art. Regardless of the route of administration selected the invention provides a compound of formula X, in unit dosage form comprising the compound either alone or in admixture with a pharmaceutically acceptable carrier appropriately selected from those known.

An effective but nontoxic quantity of the compound X is employed in treatment. The dosage regimen is selected in accordance with a variety of factors including the type, age, weight, sex, and medical condition of the mammal, the severity of symptoms of the disease being treated, the route of administration and particular compound of formula X employed. An ordinarily skilled physician or veterinarian will readily determine and prescribe the effective amount of the compound X to prevent or arrest the progress of the disease condition. In so proceeding, the physician or veterinarian could employ relatively low dosages at first, subsequently increasing the dose until a maximum resonse is obtained. For convenience, the total daily dosage may be divided and administered in portions during the day if desired.

It is understood that the compositions and methods of treatment of the present invention as described above also include the pharmacologically acceptable acid addition salts of the compounds of formula X.

For this reason U.S. Ser. No. 852,731 filed Apr. 21, 1986 which is a continuation in part of U.S. Ser. No. 745,956 filed June 17, 1985, are both hereby incorporated by reference herein.

Such variations within the skill of the art are also within the process of the present invention.

EXAMPLES

The following examples further illustrate the invention without limiting it thereto.

EXAMPLE 1

Preparation of 3-pyridinecarboxylic acid, 5-cyano-1,4-dihydro-6-methyl-2[4-pyridinylthio methyl]-4-[(2-trifluoromethyl)phenyl]-, ethyl ester 5.2 g of 90% pyridinium bromide perbromide was added in one portion to a solution of 5 g of 3-pyridinecarboxylic acid, 5-cyano-1,4-dihydro-2,6-dimethyl-4-[2-(trifluoromethyl)phenyl]-, ethyl ester and 1.2 ml pyridine in 150 ml of dry ethanol-free $CHCl_3$ at $-10°$ C. The mixture was stirred for 45 minutes at $0°$ C. and the bromide (6 g) was obtained by flash chromatography over silica gel (10% $EtAc/CH_2Cl_2$). This was dissolved in 30 ml of THF and added dropwise to a suspension of 4-mercaptopyridine, sodium salt [(prepared from 1.5 g of 4-mercapto pyridine and 0.5 g of 60% NaH in THF/DMF (1:1, 40 ml)] at $0°$ C. and the mixture was warmed to room temperature. After stirring for one hour, the reaction mixture was diluted with water and extracted with $CH_2Cl_2$. The organic extracts were washed with water, dried, and evaporated. The residue was crystallized from EtAc to give 5.1 g of 3-pyridinecarboxylic acid, 5-cyano-1,4-dihydro-6-methyl-2[4-pyridinylthiomethyl]-4-[(2-trifluoromethyl)phenyl]-, ethyl ester, mp 222°–224° C.

The following additional compounds are obtained by following the procedure described in Example 1 and selecting the requisite substrate.

EXAMPLE 2

3-Quinolinecarboxylic acid, 1,4,5,6,7,8-hexahydro-5-oxo-2-[(phenylthio)methyl]-4-[2-(trifluoromethyl)-phenyl]-, ethyl ester, mp 178°–180° C. is obtained from 3-quinolinecarboxylic acid, 1,4,5,6,7,8-hexahydro-5-oxo-2-methyl-4-[2-(trifluoromethyl)phenyl]-, ethyl ester.

EXAMPLE 3

3-Pyridinecarboxylic acid, 5-cyano-1,4-dihydro-6-methyl-2-[[4-(phenylmethyl)-1-piperazinyl]methyl]-4-[2-(trifluoromethyl)phenyl]-, ethyl ester.

EXAMPLE 4

3-Pyridinecarboxylic acid, 5-cyano-1,4-dihydro-2-[[4-(2-hydroxy-3-phenoxypropyl)-1-piperazinyl]methyl]-6-methyl-4-[2-(trifluoromethyl)phenyl]-, ethyl ester.

Calcd. for $C_{31}H_{34}F_3N_4O_4$; C, 63.80; H, 5.87; N, 9.60. Found C, 63.16; H, 5.99; N, 9.48.

mol ion m+1 584 (mass spectrum).

ir, 2203 $cm^{-1}$ (CN) 1700 $cm^{-1}$ ($CO_2Et$).

$^1H$ NMR ($CDCl_3$) δ: 8.1 (1H, $s_1$ broad NH), 6.9–7.6 (9H, m, aromatics), 5.1 (1H, s, $C_4-\underline{H}$), 4.1–3.8 (7H, m, Hs at a, b, c, d), 2.6–2.8

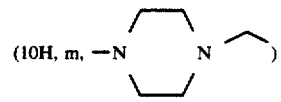

(10H, m, $-N\quad N\quad$)

2.1 (3H, s, $CH_3$) and 1.0 (3H, t, $CO_2CH_2CH_3$).

EXAMPLE 5

3-Pyridinecarboxylic acid, 5-cyano-1,4-dihydro-6-methyl-2-(4-morpholinylmethyl)-4-[2-(trifluoromethyl)phenyl]-, ethyl ester.

mp 174°–175° C.

Light yellow solid.

EXAMPLE 6

3-Pyridinecarboxylic acid, 5-cyano-2-[(3,4-dihydro-2-oxo-1(2H)-quinolinyl)methyl]-1,4-dihydro-6-methyl-4-[2-(trifluoromethyl)phenyl]-, ethyl ester.

mp 210°–211° C.

Dull olive solid.

EXAMPLE 7

3-Pyridinecarboxylic acid, 5-cyano-1,4-dihydro-6-methyl-2-[(4-phenyl-1H-imidazol-1-yl)methyl]-4-[2-(trifluoromethyl)phenyl]-, ethyl ester.

mp 276°–278° C.

White solid.

EXAMPLE 8

3-Pyridinecarboxylic acid, 5-cyano-1,4-dihydro-6-methyl-2-[(2-methyl-1H-imidazol-1-yl)methyl]-4-[2-(trifluoromethyl)phenyl]-, ethyl ester.

mp 226°–228° C.

EXAMPLE 9

3-Pyridinecarboxylic acid, 5-cyano-1,4-dihydro-2-(1H-imidazol-1-ylmethyl)-6-methyl-4-[2-(trifluoromethyl)phenyl]-, ethyl ester.

mp 216°–218° C.

White solid.

EXAMPLE 10

3-Pyridinecarboxylic acid, 5-cyano-1,4-dihydro-6-methyl-2-[(4-pyridinylthio)methyl]-4-[2-(trifluoromethyl)phenyl]-, ethyl ester.
mp 229°–230° C.
White solid.

EXAMPLE 11

3-Pyridinecarboxylic acid, 5-cyano-1,4-dihydro-6-methyl-2-[(phenylthio)methyl]-4-[2-(trifluoromethyl)phenyl]-, ethyl ester.
mp 122°–123° C.
Pale yellow solid.

What is claimed is:

1. A process for the preparation of a compound of the formula (I)

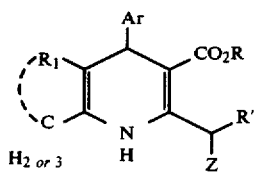

wherein Ar is aryl or heteroaryl;
R' is hydrogen, lower alkyl, or aryl;
R is straight or branched hydrocarbon chain of from two through six carbons;
$R_1$ is CN, $CO_2R_3$ wherein $R_3$ is hydrogen or lower alkyl, or is taken together with - - - , which is an optional bond to form a fused ring of the formula

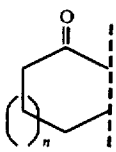

wherein n is zero or one and Z is
(1) A-$R_2$ wherein A is O or S and $R_2$ is
  (i) alkyl, straight or branched, optionally substituted by (a) hydroxy, (b) alkoxy, (c) $NR_3R_4$ wherein $R_3$ and $R_4$ are independently hydrogen or lower alkyl; (d) $S(O)_nR_5$ wherein n is zero, one or two and $R_5$ is lower alkyl, aryl, aralkyl wherein Ar is aryl and alkyl is an alkylenyl linkage straight or branched having of from one to four carbons, or heteroaryl with the proviso that $R_2$ is not $S(O)_n$ when A is S; or
  (e) $CO_2R_4$ wherein $R_4$ is hydrogen or lower alkyl;
  (ii) aryl;
  (iii) heteroaryl; or
  (iv)

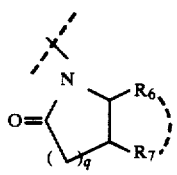

wherein q is one or two, and - - - is an optional bond; $R_6$ and $R_7$ are independently hydrogen, alkyl of from one to four carbons, alkenyl of from two to four carbons, or taken together with - - - $R_6$ and $R_7$ form

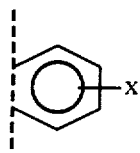

wherein X is halogen, lower alkyl, trifluoromethyl, nitro, amino, mono- or di-lower alkylamino, cyano, lower alkoxy, lower alkylthio, and the like;
(2) $NR_3R_4$ wherein $R_3$ and $R_4$ are independently hydrogen or lower alkyl; or
(3)

wherein Y is O, S, $CH_2$, CHAr wherein Ar is independently aryl, or $NR_5$ wherein $R_5$ is independently as defined above;
(4)

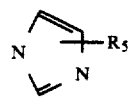

wherein $R_5$ is independently as defined above.
Which comprises (1) treating a compound of the formula (II)

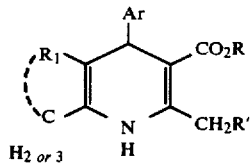

wherein Ar, R', $R_1$, and R are as defined above; with pyridinium bromide perbromide and then (2) treating the result of (1) with a compound of the formula HZ wherein Z is as defined above; wherein the treatment is at a temperature of from −50° C. to room temperature for (1) and stirred until chromatography indicates the formation of the result and wherein the treatment is at a temperature of from −20° C. to 0° C. for (2) and stirred until chromatography indicates the formation of the compound of formula I.

2. A process of claim 1 wherein the compound of the step (1) having the formula (III)

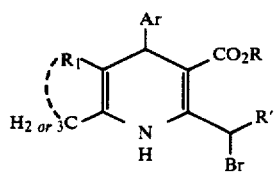

wherein Ar, R', R₁, and R are as defined above; is identified or isolated and then treated according to step 2 of claim 1.

3. A process of claim 2 wherein the step 1 is in a dry, inert solvent and in the presence of pyridine.

4. A process of claim 4 wherein the solvent is dry ethanol-free chloroform or methylene chloride.

5. A process of claim 2 wherein step 2 is in a solvent in the presence of NaH.

6. A process of claim 5 wherein the solvent of step 2 is part tetrahydrofuran and part dimethylformamide.

7. A process of claim 6 wherein each part is equal.

8. A process of claim 1 wherein Ar is 2-(trifluoromethyl)phenyl, R is ethyl, R₁ is cyano, and Z is

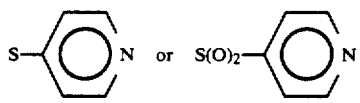

9. A process for the preparation of a compound of the formula (III)

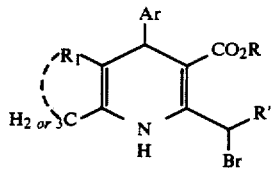

wherein

Ar is aryl or heteroaryl;

R' is hydrogen, lower alkyl or aryl;

R is straight or branched hydrocarbon chain of from two through six carbons;

R₁ is CN, CO₂R₃ wherein R₃ is hydrogen or lower alkyl, or is taken together with - - -, which is an optional bond to form a fused ring of the formula

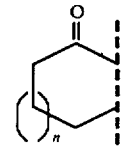

wherein n is zero or one which comprises (1) treating a compound of the formula (II)

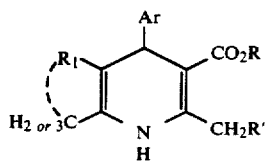

wherein Ar, R', R₁, and R are as defined above; with pyridinium bromide perbromide at a temperature of from −50° C. to room temperature and stirring until chromatography indicates the formulation of the compound of formula III.

* * * * *

UNITED STATES PATENT AND TRADEMARK OFFICE
CERTIFICATE OF CORRECTION

PATENT NO. : 4,723,014
DATED : February 2, 1988
INVENTOR(S) : KEVIN R. ANDERSON, ILA SIRCAR It is certified that error appears in the above—identified patent and that said Letters Patent is hereby corrected as shown below:

Column 11, line 60, change

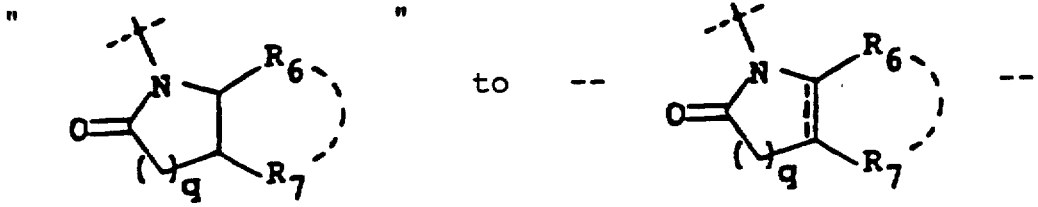

Signed and Sealed this

Fifth Day of July, 1988

Attest:

DONALD J. QUIGG

Attesting Officer

Commissioner of Patents and Trademarks